United States Patent
Chun et al.

(10) Patent No.: US 7,045,482 B2
(45) Date of Patent: May 16, 2006

(54) METHOD FOR PREPARING A HETEROPOLYACID CATALYST FROM BASIC SOLVENT TREATMENTS AND METHOD FOR PREPARING METHACRYLIC ACID USING THEREROF

(75) Inventors: Myung-Suk Chun, Seoul (KR); In Kyu Song, Kangwon-do (KR); Suk Woo Nam, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 10/452,220

(22) Filed: Jun. 3, 2003

(65) Prior Publication Data

US 2003/0233014 A1    Dec. 18, 2003

(30) Foreign Application Priority Data

Jun. 4, 2002    (KR) ...................... 10-2002-0031387

(51) Int. Cl.
  B01J 27/18    (2006.01)
  B01J 21/02    (2006.01)
  B01J 21/06    (2006.01)
  C07C 51/235  (2006.01)
(52) U.S. Cl. ...................... 502/208; 502/202; 502/204; 502/206; 502/209; 502/210; 502/211; 502/232; 502/305; 502/353; 562/532
(58) Field of Classification Search .............. 502/208, 502/209, 211, 210, 202, 204, 206, 232, 305, 502/353
See application file for complete search history.

(56) References Cited

U.S. PATENT DOCUMENTS

| | | | |
|---|---|---|---|
| 4,017,423 A | 4/1977 | White et al. | |
| 4,051,179 A | 9/1977 | Sonobe et al. | |
| 4,075,244 A | 2/1978 | Akiyama et al. | |
| 4,489,170 A | 12/1984 | Krabetz et al. | |
| 4,522,934 A * | 6/1985 | Shum et al. ................. | 502/209 |
| 5,191,116 A | 3/1993 | Yamamatsu et al. | |
| 5,198,579 A | 3/1993 | Honda et al. | |
| 5,231,226 A | 7/1993 | Hammon et al. | |
| 5,329,043 A | 7/1994 | Matsuura et al. | |
| 5,380,932 A | 1/1995 | Bielmeier et al. | |
| 5,856,259 A | 1/1999 | Watanabe et al. | |
| 6,458,740 B1 * | 10/2002 | Kasuga et al. ............... | 502/211 |
| 2004/0029724 A1 * | 2/2004 | Seo et al. | |

FOREIGN PATENT DOCUMENTS

JP    60-44042    *    3/1985

OTHER PUBLICATIONS

T. Komaya et al. "Activity Patterns of $H_3PMo_{12}O_{40}$ and its Alkali Salts for Oxidation Reactions", Chemistry Letters, pp. 1177-1180, (1983), no month.

K. Eguchi et al. "Catalytic Activity of Various 12-Molybdophosphates for Methacrolein Oxidation", Chemistry Letters, pp. 1345-1346 (1979), no month.

A.J. Perrotto et al., "Alkali Phosphomolybdates for Oxidation of Methacrolein to Methacrylic Acid", Journal of Catalysts, vol. 61, pp. 285-288 (1980), no month.

M. Misono et al., "Oxidizing Power as the Prime Factor Controlling HTE Catalytic Activity of $H_3PW_xMo_{12-x}O_{40}$ for Oxidation of Methacrolein", Chemistry Letters, pp. 53-56, (1982), no month.

Y. Konishi et al., "Oxidation of Methacrolein to Methacrylic Acid Over 12-Molybdophosphoric Acid", Journal of Catalysis, vol. 77, pp. 169-179, (1982), no month.

J.J. Kim et al., "Oxidation of Methacrolein and Isomerization of n-Butene Over Heteropoly Compounds", Chem. Eng. Commun., vol. 34, pp. 49-63, (1985), no month.

N. Mizuno et al., "Oxidation of Methacrylaldehyde Over 12-Molybdophosphoric Acid and its Alkali Salts", Bull. Chemical Soc. Japan, vol. 64, pp. 343-247 (1991), no month.

M. Ai, "Oxidation of Methacrolein to Methacrylic Acid on $V_2O_5$-$P_2O_5$ Based Catalysts", Journal of Catalysis, vol. 116, pp. 23-30 (1989), no month.

F. Cavani et al., "Enhancement of Catalytic Activity of the Ammomium Potassium Salt of 12-Molybdophosphoric Acid by Iron Ion Addition for the Oxidation of Isobutane to Methacrylic Acid", Catalysis Letters, vol. 32, pp. 215-226, (1995), no month.

N. Mizuno et al., "Direct Oxidation of Isobutane Into Methacrylic Acid and Methacrolein Over $Cs_{2.5}Ni_{0.08}$-Substituted $H_3PMo_{12}O_{40}$", J. Chem. Soc., Chem. Commun., pp. 1411-1412, (1994), no month.

W. Li et al., "Catalytic Oxidation of Isobutane to Methacrylic Acid with Molecular Oxygen Over Activated Pyridinium, 12-Molybdophosphate", Catalysis Letters, vol. 46, pp. 261-265, (1997), no month.

* cited by examiner

Primary Examiner—Wayne A. Langel
(74) Attorney, Agent, or Firm—Finnegan, Henderson, Farabow, Garrett & Dunner, LLP

(57)    ABSTRACT

The present invention relates to a method for preparing a heteropolyacid catalyst and method for preparing methacrylic acid using thereof. More particularly, the present invention relates to a method for preparing heteropolyacid catalyst, which is produced by the recrystallization of a heteropolyacid and/or its salt dissolved in a basic organic solvent and heat-treatment, and further to a method for preparing metachrylic acid using thereof, wherein the use of the heteropolyacid catalyst increases the activity of oxidation reaction induced by the modified electronic properties of heteropolyanions and provides high efficiency production of methacrylic acid from methacrolein, since the basic property of solvent inhibits peculiar acidic property of heteropolyacid.

5 Claims, No Drawings

METHOD FOR PREPARING A HETEROPOLYACID CATALYST FROM BASIC SOLVENT TREATMENTS AND METHOD FOR PREPARING METHACRYLIC ACID USING THEREROF

FIELD OF THE INVENTION

The present invention relates to a method for preparing a heteropolyacid catalyst and method for preparing methacrylic acid using thereof. More particularly, the present invention relates to a method for preparing heteropolyacid catalyst, wherein it is produced by the recrystallization of the heteropolyacid and/or its salt dissolved in a basic organic solvent and the heat-treatment, and further to a method for preparing metachrylic acid using thereof, wherein the use of the heteropolyacid catalyst increases the activity of oxidation reaction induced by the modified electronic properties of heteropolyanions and provides high efficiency production of methacrylic acid from methacrolein, since the basic property of solvent inhibits peculiar acidic property of heteropolyacid.

Molecular weight of heteropolyacid is ca. 1,000 g or higher per heteropolyanion, even if it varies with basic structures. Heteropolyacid is an inorganic polyacid and has 10 $m^2/g$ or less of surface area. Further, heteropolyacid is well dissolved in polar organic solvents such as water, alcohols, and amines and is a catalyst having bifunctional characteristics for acid as well as oxidation catalysis. When heteropolyacid catalyst acts as an acid catalyst, an acid catalytic reaction proceeds at the Brönsted acidity of heteropolyacid. On the other hand, when heteropolyacid catalyst acts as an oxidation catalyst, the reaction in which oxygen participates as a redox (reduction and oxidation) carrier performs on the surface of the catalyst and the reaction in which electrons participate does in the bulk of the catalyst (T. Komaya, M. Misono, Chem. Lett., 1177 (1983)). The method for producing methacrylic acid through the oxidation of methacrolein is a typical surface-type catalytic reaction.

A method for preparing methacrylic acid from methacrolein in the presence of heteropolyacid was first reported in 1977 (J. F. White, J. R. Rege, U.S. Pat. No. 4,017,423 (1977)). U.S. Pat. Nos. 4,051,179 and 4,075,244 disclose processes for the preparation of methacrylic acid by catalytic oxidization of methacrolein in the gas phase with molecular oxygen to form methacrylic acid in the presence of a heteropolyacid catalyst containing molybdenum(Mo)-phosphorus(P)-vanadium(V) and more other metals. U.S. Pat. No. 5,198,579 of T. Honda, N. Horiuchi, J. Kitagawa, M. Murakami, K. Kawahara, H. Io also discloses that heteropolyacid catalysts containing molybdenum(Mo)-phosphorus(P)-vanadium(V) and more other metals exhibit an efficient oxidation activity for methacrolein conversion. U.S. Pat. No. 5,231,226 further discloses a process for the catalytic gas phase oxidation of methacrolein to methacrylic acid in the presence of a heteropolyacid catalyst of which a method for the preparation is taught in U.S. Pat. No. 5,856,259. There have been many reports on similar heteropolyacid catalysts and their preparation methods. The heteropolyacid catalysts considered useful in producing methacrylic acid from methacrolein, according to these reports, are those which contain phosphorus(P) or arsenic (As) as a central heteroatom; and molybdenum(Mo) and/or vanadium(V) as a polyatom; and cesium(Cs), copper(Cu) and/or bismuth(Bi) and the like as a cation; or those prepared by impregnating heteropolyacid onto a support (K. Eguchi, I. Aso, N. Yamazoe, T. Seiyama, Chem. Lett., 1345 (1979); A. J. Perrotto, R. B. Bjorklund, J. T. Higgins, C. L. Kibby, J. Catal., 61, 285 (1980); M. Misono, T. Komaya, H. Sekiguchi, Y. Yoneda, Chem. Lett., 53 (1982); Y. Konishi, K. Sakata, M. Misono, Y. Yoneda, J. Catal., 77, 169(1982); J.-J. Kim, W. Y. Lee, H.-K. Rhee, Chem. Eng. Comm., 34, 49 (1985); and N. Mizuno, T. Watanabe, M. Misono, Bull. Chem. Soc. Japan, 64, 243 (1991)). Further, there have been reports on using oxidation catalysts containing $V_2O_5$—$P_2O_5$ components in the conversion of methacrolein to methacrylic acid (M. Ai, J. Catal., 116, 23 (1989)) and those containing Mo—W—P—Sb components (R. Krabetz, M. Schwarzmann, U.S. Pat. No. 4,489,170 (1984)).

There has been also a report on a process for preparing methacrylic acid by direct oxidation of isobutane in the presence of molecular oxygen with heteropolyacid. The catalysts used in these reactions are heteropolyacid catalysts containing phosphorus(P)-arsenic(As)-molybdenum(Mo)-vanadium(V)-other metals (S. Yamamatsu, T. Yamaguchi, U.S. Pat. No. 5,191,116 (1993); I. Matsuura, Y. Aoki, U.S. Pat. No. 5,329,043 (1994); and E. Bielmeier, T. Haeberle, H.-J. Siegert, W. Gruber, U.S. Pat. No. 5,380,932 (1995)). There have been also reported that 12-molybdophosphoric acid salt substituted with cations such as ammonium, potassium, iron and the like (F. Cavani, E. Etienne, M. Favaro, A. Galli, F. Trifio, Catal. Lett., 32, 215 (1995)), 12-molybdophosphates with cations such as cesium and nickel (N. Mizuno, T. Tateishi, M. Iwamoto, J. Chem. Soc. Chem. Comm., 1411 (1994)), pyridium salt of 12-molybdophosphoric acid catalyst (W. Li, W. Ueda, Catal. Lett., 46, 261 (1997)) etc. are suitable for the oxidation reaction of isobutane. The heteropolyacid catalysts used in the catalytic oxidation of isobutene are very similar to those used in the oxidation of methacrolein since the activity of the oxidation reaction over heteropolyacids may be generally controlled by changing central heteroatom, polyatom, and/or cations.

Accordingly, conventional heteropolyacid catalysts have been used in the oxidation of methacrolein by controlling the redox (reduction and oxidation) characteristics with changes of components. However, the present invention provides the use of basic solvent to modify electronic properties of heteropolyanions, and thus, increases the activity of the oxidation reaction and inhibits peculiar acidic property of heteropolyacids to enhance the efficiency of the catalytic oxidation reaction. Therefore, the method described in the present invention is different from the conventional ones.

SUMMARY OF THE INVENTION

The present invention was completed by establishing high efficiency production of methacrylic acid, through oxidation reaction of methacrolein in the presence of a heteropolyacid catalyst, which is prepared by comprising the steps of dissolving the heteropolyacid and/or its salt in a basic organic solvent, recrystallizing and heat-treating the result to increase the activity of heteropolyacid catalyst in the oxidation reaction induced by the electronic properties of heteropolyanions and provide high efficiency production of methacrylic acid from methacrolein, since the basic property of solvent inhibits peculiar acidic property of heteropolyacid.

Accordingly, an object of the present invention is to provide a process for preparing a heteropolyacid catalyst for the synthesis of methacrylic acid through gas phase catalytic oxidation of methacrolein. Another object of the present invention is to provide a process for preparing methacrylic acid using thus prepared heteropolyacid catalyst.

DETAILED DESCRIPTION OF THE INVENTION

As set forth hereinabove, the present invention relates to a process for preparing a heteropolyacid catalyst by dissolving heteropolyacid, its salt or a mixture thereof in a basic organic solvent, recrystallizing and heat-treating at 50 to 450° C.

In the process for preparing methacrylic acid through gas phase catalytic oxidation of methacrolein, the present invention relates further to provide a process for preparing methacrylic acid in the presence of the above-prepared heteropolyacid catalyst. The present invention is described in detail hereunder.

The present invention is to provide a process for preparing a heteropolyacid catalyst by dissolving heteropolyacid and/or its salt in a basic organic solvent, followed by the recrystallization and heat-treatment at a high temperature and process for preparing methacrylic acid through the oxidation of methacrolein in the presence of the heteropolyacid catalyst. The process for preparing a heteropolyacid catalyst is described in more detail as follows.

Heteropolyacid and/or its salt is dissolved in a basic organic solvent of which amount is not particularly limited and can use the least amount sufficient to dissolve heteropolyacid and/or its salt. However, it is preferable to dissolve 0.1 to 50 wt. % of heteropolyacid and/or its salt in 99.9 to 50 wt. % of the basic organic solvent. The heteropolyacid and/or its salt may be purchased or prepared by conventional methods. It is preferable to perform heat-treatment at a temperature of 300° C. or higher to remove moisture before dissolving it in the solvent. The heteropolyacid is an inorganic polyacid that contains molybdenum (Mo), tungsten(W), vanadium(V), niobium(Nb) and the like as a polyatom; and phosphorus(P), silicon(Si), germanium (Ge), arsenic(As), boron(B), cobalt(Co), and the like as a central heteroatom. Heteropolyacid can be selected at least one from the group consisting of 12-molybdophosphoric acid($H_3PMo_{12}O_{40}$), 12-tungstophosphoric acid ($H_3PW_{12}O_{40}$), 12-tungstosilicic acid($H_4SiW_{12}O_{40}$), 12-molybdotungstophosphoric acid($H_3PMo_{12-x}W_xO_{40}$, x=0–12), 12-molybdovanadophosphoric acid($H_{3+x}PMo_{12-x}V_xO_{40}$, x=0–12), 18-molybdovanadophosphoric acid($H_{6+x}P_2Mo_{18-x}V_xO_{62}$, x=0–18), and 18-tungstoniobophosphoric acid($H_{6+x}P_2W_{18-x}Nb_xO_{62}$, x=0–18). As a salt of heteropolyacid, a part of or all protons of heteropolyacid may be substituted with at least one metal element chosen from group 1A to 7A, group 1B to 5B, and group 8B in the periodic table, preferably sodium(Na), cesium(Cs), copper (Cu), iron(Fe), bismuth(Bi) and the like. Examples of basic organic solvent include aniline, dimethylformamide, quinoline, tetrahydrofuran, dimethylacetamide, pyridine, dimethylsulfoxide, ethylamine, N-methylpyrrolidone and butylamine.

After heteropolyacid and/or its salt is dissolved in a basic solvent, a mixture is stirred for 10 min. to 24 h and recrystallized by evaporating under the atmospheric pressure or vacuum drying to obtain crude solid product. The crude product is then heat-treated at 50 to 450° C., preferably 200 to 450° C., under the air flow to give the desired heteropolyacid catalyst. If the temperature is below 50° C., the electronic property of heteropolyanions be hardly achieved. In contrast, if it is above 450° C., the catalytic property becomes lost because the structure of the heteropolyacid is destroyed due to its decomposition.

In particular, the present invention is characterized in that it requires use of a basic organic solvent and heat-treatment process at a high temperature in the process for preparing heteropolyacid catalyst. Typical heteropolyacid catalyst works as an acidic catalyst as well as an oxidation catalyst. According to the present invention, heteropolyacid and/or its salt is dissolved in a basic organic solvent to induce a strong interaction between them by allowing a strong binding of the basic solvent to heteropolyacid. The remaining basic solvent still bonded to the crude solid heteropolyacid catalyst after recrystallization under the atmospheric pressure or vacuum-dry is removed by heat-treatment at a high temperature to modify electronic properties of heteropolyanions. Thus, heteropolyacid catalysts having such electronic properties may be efficiently used for the oxidation reactions. In the use of heteropolyacid catalysts having bifunctional properties for acid as well as oxidation catalysis, the heteropolyacid catalyst of the present invention exhibits higher oxidation catalysis since the acidic characteristics of the heteropolyacid is restrained with using of the basic solvent. The electronic properties of the heteropolyacid catalyst can be modified effectively when the strong interaction between the heteropolyacid and the basic material is deformed by the heat-treatment.

The heteropolyacid catalyst prepared according to the present invention shows many differences in characteristics as compared to the conventional heteropolyacid catalyst. For example, the heteropolyacid catalyst of the present invention shows a shift in wave number in Infrared (IR) spectrum, a chemical shift in Nuclear Magnetic Resonance (NMR) spectrum and obviously a different electron binding energy around the polyatoms in X-ray Photoelectron Spectroscopy (XPS), as compared to the conventional ones.

Since such electronic properties of the heteropolyacid catalyst prepared in the present invention are more effective for an oxidation reaction, the heteropolyacid catalyst becomes useful for the oxidation of methacrolein.

Further, the present invention includes a process for preparing methacrylic acid using the heteropolyacid catalyst prepared as described above.

The present invention will now be explained in more detail with reference to the following examples, but it is to be understood that the present invention is not restricted thereto and various modifications are possible within the scope of the invention.

EXAMPLE 1

Preparation of Heteropolyacid Catalyst

A predetermined amount of 12-molybdophosphoric acid ($H_3PMo_{12}O_{40}$) was heat-treated at 300° C. to remove moisture therein. 2 g of the heat-treated 12-molybdophosphoric acid was then dissolved in 50 cc of tetrahydrofuran. Thus obtained solution was stirred for 10 hours at room temperature, placed at room temperature for additional 2 hours, and vacuum-dried to remove the solvent, tetrahydrofuran. The residue was placed into an electric furnace for heat-treatment kept at 300° C. with an air stream of 50 cc per minute, and 12-molybdophosphoric acid catalyst treated with tetrahydrofuran was finally obtained.

The product was subjected to an analysis by means of IR and Brunauer-Emmet-Teller (BET) and the result is summarized in Table 1.

TABLE 1

| Catalyst | IR wave number(cm$^{-1}$) | | | | Surface area[1] (m$^2$/g) |
|---|---|---|---|---|---|
| | P—O | Mo=O | Mo—O—Mo | | |
| 12-molybdophosphoric acid (H$_3$PMo$_{12}$O$_{40}$) | 1064 | 961 | 866 | 781 | 4.0 |
| Example 1 | 1064 | 975 | 867 | 783 | 14.0 |

[1] Surface area was calculated from the amount of nitrogen adsorption determined using ASAP-2000 (Micromeritics, U.S.A.) from the linear form of BET equation.

As shown in Table 1, it is noted that the heteropolyacid catalyst prepared in Example 1 of the present invention exhibited higher wave frequency for Mo=O bond, compared to 12-molybdophosphoric acid which was not treated with tetrahydrofuran, while the other wave frequencies of P—O and Mo—O—Mo were same for both heteropolyacid catalysts. Thus, it shows that the treatment of the heteropolyacid with a basic solvent resulted in the change of the electronic properties of the heteropolyacid catalyst.

Further, the surface area of the heteropolyacid catalyst of the present invention was increased by at least 3 times as compared to that of 12-molybdophosphoric acid and it was predicted that the heteropolyacid catalyst is more efficient for the oxidation of methacrolein than the conventional heteropolyacid catalyst including 12-molybdophosphoric acid catalyst.

The heteropolyacid catalyst prepared in Example 1 was also subjected to analysis by means of NMR and XPS in order to determine other changes in properties. The result is summarized in Table 2.

TABLE 2

| Cataystt | NMR[1] Chemical shift (ppm) | XPS Mo binding energy (eV) | |
|---|---|---|---|
| | | Mo 3d$_{3/2}$ | Mo 3d$_{5/2}$ |
| 12-molybdophosphoric acid (H$_3$PMo$_{12}$O$_{40}$) | −2.7 | 233.8 | 230.6 |
| Example 1 | −5.0 | 233.4 | 230.2 |

[1]: The $^{31}$P chemical shifts are in ppm with respect to H$_3$PO$_4$

As shown in Table 2, the heteropolyacid catalyst prepared in Example 1 of the present invention was found to have a different $^{31}$P chemical shift from 12-molybdophosphoric acid which was not treated with tetrahydrofuran. It imports that the characteristics of the heteropolyacid catalyst of the present invention is significantly different from the conventional one. The heteropolyacid catalyst of the present invention was also found to have a lower Mo binding energy compared to that of 12-molybdophosphoric acid which was not treated with tetrahydrofuran. It is noted that the electron density around molybdenum in the heteropolyacid catalyst of the present invention was increased. Because the heteropolyacid catalyst of the present invention is in a more reduced state than that of 12-molybdophosphoric acid catalyst, the heteropolyacid catalyst of the present invention is more effective for the oxidation reaction of the present invention.

EXAMPLE 2

Preparation of Heteropolyacid Catalyst

A predetermined amount of 12-tungtophosphoric acid (H$_3$PW$_{12}$O$_{40}$) was heat-treated at 300° C. to remove moisture therein. 2 g of heat-treated 12-tungtophosphoric acid was then dissolved in 50 cc of tetrahydrofuran. A solution was stirred for 10 hours at room temperature, placed at room temperature for additional 2 hours, and vacuum-dried to remove the solvent, tetrahydrofuran. The residue was placed into an electric furnace for heat-treatment by maintaining a temperature at 350° C. and flowing 50 cc of air per minute. 12-Tungstophosphoric acid catalyst treated with tetrahydrofuran was then produced.

EXAMPLE 3

Preparation of Heteropolyacid Catalyst

A predetermined amount of copper-exchanged 10-molybdo-2-vanadophosphoric acid(Cu$_{5/2}$PMo$_{10}$V$_2$O$_{40}$) was heat-treated at 300° C. to remove moisture therein. 2 g of heat-treated copper-exchanged 10-molybdo-2-vanadophosphoric acid was then dissolved in 50 cc of dimethylacetamide. A solution was stirred for 5 hours at room temperature, placed at room temperature for additional 2 hours, and vacuum-dried to remove the solvent, dimethylacetamide. The residue was placed into an electric furnace for heat-treatment by maintaining a temperature at 300° C. and flowing 50 cc of air per minute. Copper-exchanged 10-molybdo-2-vanadophosphoric acid catalyst treated with dimethylacetamide was then produced.

EXAMPLE 4

Preparation of Heteropolyacid Catalyst

A predetermined amount of 12-molybdophosphoric acid (H$_3$PMo$_{12}$O$_{40}$) was heat-treated at 300° C. to remove moisture therein. 2 g of heat-treated 12-molybdophosphoric acid was then dissolved in a mixture of 25 cc of aniline and 25 cc of quinoline. A solution was stirred for 10 hours at room temperature, placed at room temperature for additional 2 hours, and vacuum-dried to remove the solvent. The residue was placed into an electric furnace for heat-treatment by maintaining a temperature at 300° C. and flowing 50 cc of air per minute. 12-Molybdophosphoric acid catalyst treated with aniline and quinoline was then produced.

EXAMPLES 5–6

Preparation of Heteropolyacid Catalyst

A predetermined amount of 11-molybdo-1-vanadophosphoric acid(H$_4$PMo$_{11}$V$_1$O$_{40}$) was heat-treated at 300° C. to remove moisture therein. 2 g of heat-treated 11-molybdo-1-vanadophosphoric acid was then dissolved in 50 cc of quinoline (Example 5) or 50 cc of aniline (Example 6). Each solution was stirred for 10 hours at room temperature, placed at room temperature for additional 2 hours, and vacuum-dried to remove the solvent. The residue was placed into an electric furnace for heat-treatment by maintaining a temperature at 300° C. and flowing 50 cc of air per minute. 11-Molybdo-1-vanadophosphoric acid catalyst treated with quinoline (Example 5) or with aniline (Example 6) was then produced.

EXAMPLE 7

Preparation of Heteropolyacid Catalyst

12-Molybdophosphoric acid catalyst was prepared in the same manner as in Example 3, except that 12-molybdophosphoric acid of which protons were exchanged with cesium and lithium ($Cs_{2.85}Li_{0.15}PMo_{12}O_{40}$) was used and tetrahydrofuran as a basic organic solvent. The heat-treatment temperature was 350° C.

EXAMPLE 8

Preparation of Heteropolyacid Catalyst

12-Molybdophosphoric acid catalyst was prepared in the same manner as in Example 4, except that a mixture of quinoline and pyridine (1:1) was used as a basic organic solvent.

EXAMPLES 9–11

Preparation of Heteropolyacid Catalyst

6-Molybdo-6-tungstophosphoric acid catalyst (Example 9) and 10-molybdo-2-vanadophosphoric acid catalyst (Example 10) were prepared in the same manner as in Example 2, except that 6-molybdo-6-tungstophosphoric acid (Example 9) and 10-molybdo-2-vanadophosphoric acid (Example 10) were used and the heat-treatment temperature was 320° C.

Further, 6-Molybdo-6-tungstophosphoric acid/10-molybdo-2-vanadophosphoric acid catalyst (Example 11) was prepared in the same manner as in Example 2, except that a mixture of 50 wt. % of 6-molybdo-6-tungstophosphoric acid and 50 wt. % of 10-molybdo-2-vanadophosphoric acid (Example 11) was used.

Experimental Example 1

Preparation of Methacrylic Acid

In order to determine catalytic activities of the heteropolyacid catalysts of the present invention for the catalytic gas phase oxidation of methacrolein to methacrylic acid, the heteropolyacid catalysts prepared in the above Examples were used for the production of methacrylic acid as follows:

0.1 g of the heteropolyacid catalyst prepared in Example 5 was placed into a tubular Pyrex reactor for gas phase oxidation and heat-treated at 300° C. by flowing 50 cc of air per minute. Methacrolein was sufficiently vaporized while the temperature was set at 300° C. and then a gas phase methacrolein was fed into a reactor by using air as a carrier gas at a contact time(W/F) of 84 catalyst(g)·hr/methacrolein (mole) [i.e., the value (W/F) was obtained by dividing the weight of catalyst(W (g)) by the molar flow rate of methacrolein (F (mole/hr))]. The mole ratio of methacrolein to air introduced to the reactor was constantly maintained at 1.6:98.4. After introducing methacrolein to the catalyst placed into the reactor, the reaction was performed at 280° C. After 3 hours when it reached steady-state, the products were analyzed by gas chromatography. The catalytic activity of the catalyst is summarized in Table 3.

Experimental Example 2

Preparation of Methacrylic Acid

Methacrylic acid was prepared in the same manner as in Experimental Example 1, except that the heteropolyacid catalyst prepared in Example 6 was used. The catalytic activity of the catalyst is summarized in Table 3.

TABLE 3

| Catalyst | Conversion[1] (%) | Selectivity[2] (%) Methacrylic acid | Acetic acid | $CO + CO_2$ + others | Yield[3] (%) |
|---|---|---|---|---|---|
| 11-molybdo-1-vanadophosphoric acid ($H_4PMo_{11}V_1O_{40}$) | 2.73 | 34.2 | 43.1 | 22.7 | 0.93 |
| Example 5 | 3.40 | 36.4 | 34.1 | 29.4 | 1.24 |
| Example 6 | 4.12 | 38.0 | 36.3 | 25.7 | 1.57 |

Reaction temperature = 280° C., contact time(W/F) = 84 catalyst(g) . hr/methacrolein(mole), Methacrolein:air = 1.6:98.4% by mole

[1] Conversion of methacrolein =

$$\frac{[(\text{No. of moles of methacrolein at reactor inlet}) - (\text{No. of moles of methacrolein at reactor outlet}]}{(\text{No. of moles of methacrolein at reactor inlet})} \times 100 \ (\%)$$

[2] Selectivity of product = [(No. of moles of a target product)/(Total No. of moles of products)] × 100 (%)
[3] Yield of methacrylic acid = [(Conversion of methacrolein) × (Selectivity of methacrylic acid)] × 100 (%)
[4] The yield of other products were negligible being lower than 1% of total selectivity.

As shown in Table 3, the heteropolyacid catalysts prepared in Examples 5 and 6 exhibited superior conversion of methacrolein, and enhanced selectivity and yield toward methacrylic acid to 11-molybdo-1-vanadophosphoric acid catalyst. In particular, the acid catalytic reaction to produce acetic acid was reduced with the heteropolyacid catalysts prepared in Examples 5 and 6 and relatively, the oxidation reaction was increased.

Experimental Example 3

Preparation of Methacrylic Acid

In order to determine the catalytic activity of the heteropolyacid catalyst prepared in Example 7 for the catalytic gas phase oxidation of methacrolein to methacrylic acid, the heteropolyacid catalyst was used for the production of methacrylic acid as follows:

1.5 g of the heteropolyacid catalyst prepared in Example 7 was placed into a tubular Pyrex reactor for gas phase oxidation and heat-treated at 350° C. by flowing 50 cc of air per minute. Methacrolein was sufficiently vaporized while the temperature was set at 320° C. and then a gas phase methacrolein was fed into a reactor by using air as a carrier gas. The mole ratio of methacrolein:water:air introduced to the reactor was constantly maintained at 1.3:28.0:70.7 and a contact time(W/F) was 1,400 catalyst(g)·hr/methacrolein (mole). After introducing methacrolein to the catalyst placed into the reactor, the reaction was performed at 320° C. After 3 hours when it reached steady-state, the products were analyzed by gas chromatography. The catalytic activity of the catalyst is summarized in Table 4.

TABLE 4

| Catalyst | Conversion[1] (%) | Selectivity[2] (%) | | | Yield[3] (%) |
| --- | --- | --- | --- | --- | --- |
| | | Methacrylic acid | Acetic acid | $CO + CO_2$ + others | |
| 12-molybdophosphoric acid ($CS_{2.85}Li_{0.15}PMo_{12}O_{40}$) | 61.8 | 23.5 | 16.3 | 60.2 | 14.5 |
| Example 7 | 68.2 | 29.3 | 11.2 | 59.5 | 20.0 |

Reaction temperature = 320° C., contact time(W/F) = 1,400 catalyst(g) · hr/methacrolein(mole), Methacrolein:water:air = 1.3:28.0:70.7% by mole

[1] Conversion of methacrolein =

$$\frac{[(\text{No. of moles of methacrolein at reactor inlet}) - (\text{No. of moles of methacrolein at reactor outlet})]}{(\text{No. of moles of methacrolein at reactor inlet})} \times 100 \ (\%)$$

[2] Selectivity of product = [(No. of moles of a target product)/(Total No. of moles of products)] × 100 (%)
[3] Yield of methacrylic acid = [(Conversion of methacrolein) × (Selectivity of methacrylic acid)] × 100 (%)

As shown in Table 4, the heteropolyacid catalysts prepared by treating with a basic solvent in Example 7 exhibited superior conversion of methacrolein, and enhanced selectivity and yield toward methacrylic acid to 12-molybdophosphoric acid salt.

Experimental Example 4

Preparation of Methacrylic Acid

In order to determine the catalytic activity of the heteropolyacid catalyst prepared in Example 8 for the catalytic gas phase oxidation of methacrolein to methacrylic acid, the heteropolyacid catalyst was used for the production of methacrylic acid as follows:

1.5 g of the heteropolyacid catalyst prepared in Example 8 was placed into a tubular Pyrex reactor for gas phase oxidation and heat-treated at 300° C. by flowing 50 cc of air per minute. Methacrolein was sufficiently vaporized while the temperature was set at 300° C. and then a gas phase methacrolein was fed into a reactor by using air as a carrier gas. The mole ratio of methacrolein:water:air introduced to the reactor was constantly maintained at 1.3:28.0:70.7 and a contact time(W/F) was 1,400 catalyst(g)·hr/methacrolein (mole). After introducing methacrolein to the catalyst placed into the reactor, the reaction was performed at 300° C. After 3 hours when it reached steady-state, the products were analyzed by gas chromatography. The catalytic activity of the catalyst is summarized in Table 5.

TABLE 5

| Catalyst | Conversion[1] (%) | Selectivity[2] (%) | | | Yield[3] (%) |
|---|---|---|---|---|---|
| | | Methacrylic acid | Acetic acid | $CO + CO_2 +$ others | |
| 12-molybdophosphoric acid ($H_3PMo_{12}O_{40}$) | 40.5 | 24.4 | 17.3 | 58.3 | 9.9 |
| Example 8 | 46.2 | 30.2 | 13.2 | 56.6 | 14.0 |

Reaction temperature = 300° C., contact time(W/F) = 1,400 catalyst(g) · hr/methacrolein(mole), Methacrolein:water:air = 1.3:28.0:70.7% by mole

[1] Conversion of methacrolein =

$$\frac{[(\text{No. of moles of methacrolein at reactor inlet}) - (\text{No. of moles of methacrolein at reactor outlet})]}{(\text{No. of moles of methacrolein at reactor inlet})} \times 100 \ (\%)$$

[2] Selectivity of product = [(No. of moles of a target product)/(Total No. of moles of products)] × 100 (%)
[3] Yield of methacrylic acid = [(Conversion of methacrolein) × (Selectivity of methacrylic acid)] × 100 (%)

As shown in Table 5, the heteropolyacid catalysts prepared by treating with a basic solvent in Example 8 exhibited superior conversion of methacrolein, and enhanced selectivity and yield toward methacrylic acid as compared to those of 12-molybdophosphoric acid catalyst.

Experimental Examples 5 to 7

Preparation of Methacrylic Acid

In order to determine the catalytic activity of the heteropolyacid catalysts prepared in Examples 9 to 11 for the catalytic gas phase oxidation of methacrolein to methacrylic acid, the heteropolyacid catalyst was used for the production of methacrylic acid as follows:

1.5 g of each heteropolyacid catalyst prepared in Examples 9 to 11 was placed into a tubular Pyrex reactor for gas phase oxidation and heat-treated at 320° C. by flowing 50 cc of air per minute. Methacrolein was sufficiently vaporized while the temperature was set at 300° C. and then a gas phase methacrolein was fed into a reactor by using air as a carrier gas. The mole ratio of methacrolein:water:air introduced to the reactor was constantly maintained at 1.3:28.0:70.7 and a contact time(W/F) was 1,400 catalyst (g)·hr/methacrolein(mole). After introducing methacrolein to the catalyst placed into the reactor, the reaction was performed at 300° C. After 3 hours when it reached steady-state, the products were analyzed by gas chromatography. The catalytic activity of the catalyst is summarized in Table 5.

TABLE 6

| Catalyst | Conversion[1] (%) | Selectivity[2] (%) | | | Yield[3] (%) |
|---|---|---|---|---|---|
| | | Methacrylic acid | Acetic acid | $CO + CO_2 +$ others | |
| Example 9 | 41.8 | 25.2 | 17.2 | 57.6 | 10.5 |
| Example 10 | 52.9 | 33.4 | 14.2 | 52.4 | 17.7 |
| Example 11 | 46.9 | 30.4 | 15.0 | 54.6 | 14.3 |

Reaction temperature = 300° C., contact time(W/F) = 1,400 catalyst(g) · hr/methacrolein(mole), Methacrolein:water:air = 1.3:28.0:70.7% by mole TABLE 6-continued

| Catalyst | Conversion[1] (%) | Selectivity[2] (%) | | | Yield[3] (%) |
|---|---|---|---|---|---|
| | | Methacrylic acid | Acetic acid | CO + CO$_2$ + others | |

[1] Conversion of methacrolein =

$$\frac{[(\text{No. of moles of methacrolein at reactor inlet}) - (\text{No. of moles of methacrolein at reactor outlet}]}{(\text{No. of moles of methacrolein at reactor inlet})} \times 100 \ (\%)$$

[2] Selectivity of product = [(No. of moles of a target product)/(Total No. of moles of products)] × 100 (%)
[3] Yield of methacrylic acid = [(Conversion of methacrolein) × (Selectivity of methacrylic acid)] × 100 (%)

As shown in Table 6, conversion of methacrolein, selectivity and yield toward methacrylic acid over the heteropolyacid catalyst prepared in Example 11 lied halfway between each heteropolyacid catalyst.

As described above, heteropolyacid catalysts of the present invention provide excellent activity for the oxidation of methacrolein to obtain methacrylic acid, since the heteropolyacid catalysts produced by the recrystallization of the heteropolyacid and/or its salt dissolved in a basic organic solvent and the heat-treatment retain the modified electronic properties of heteropolyanions.

What is claimed is:

1. A method for preparing a heterpolyacid catalyst comprising the steps of: heat-treating heteropolyacid, its salt or a mixture thereof at a temperature of 300° C. or higher; dissolving the heat-treating heteropolyacid, its salt or a mixture thereof in a basic organic solvent; recrystallizing the dissolved heteropolyacid, its salt or a mixture thereof; and heat-treating the recrystallized heteropolyacid, its salt or a mixture thereof at 50 to 450° C.

2. The method for preparing a heterpolyacid catalyst in claim 1, wherein said heteropolyacid is at least one selected from the group consisting of 12-molybdophosphoric acid (H$_3$PMo$_{12}$O$_{40}$), 12-tungstophosphoric acid(H$_3$PW$_{12}$O$_{40}$), 12-tungstosilicic acid(H$_4$SiW$_{12}$O$_{40}$), 12-molybdotungstophosphoric acid(H$_3$PMo$_{12-x}$W$_x$O$_{40}$, x=0–12), 12-molybdovanadophosphoric acid(H$_{3+x}$PMo$_{12-x}$V$_x$O$_{40}$, x=0–12), 18-molybdovanadophosphoric acid(H$_{6+x}$P$_2$Mo$_{18-x}$V$_x$O$_{62}$, x=0–18), and 18-tungstoniobophosphoric acid(H$_{6+x}$P$_2$W$_{18-x}$Nb$_x$O$_{62}$, x=0–18).

3. The method for preparing a heterpolyacid catalyst in claim 1, wherein said salt of heteropolyacid is the heteropolyacid of which a part of or all protons are substituted with at least one metal element selected from the group consisting of elements of 1A to 7A, group 1B to 5B, and group 8B in the heat-treated periodic table.

4. The method for preparing a heterpolyacid catalyst in claim 1, wherein said basic solvent is at least one selected from the group consisting of aniline, dimethylformamide, quinoline, tetrahydrofuran, dimethylacetamide, pyridine, dimethylsulfoxide, ethylamine, N-methylpyrrolidone and butylamine.

5. The method for preparing a heterpolyacid catalyst in claim 1, wherein said recrystallization is performed at room temperature at atmospheric pressure or under a dry vacuum.

* * * * *

UNITED STATES PATENT AND TRADEMARK OFFICE
CERTIFICATE OF CORRECTION

| | | |
|---|---|---|
| PATENT NO. | : 7,045,482 B2 | Page 1 of 1 |
| APPLICATION NO. | : 10/452220 | |
| DATED | : May 16, 2006 | |
| INVENTOR(S) | : Myung-Suk Chun, In Kyu Song and Suk Woo Nam | |

It is certified that error appears in the above-identified patent and that said Letters Patent is hereby corrected as shown below:

Title Page:

Item 54, Title, line 5, "THEREROF" should read --THEREOF--

Item 57, Abstract, line 8, "metachrylic" should read --methacrylic--

Col. 1, Line 5, "THEREROF" should read --THEREOF--

Claim 1, column 13, line 31, "heterpolyacid" should read --heteropolyacid--

Claim 1, column 13, line 34, "heat-treating" should read --heat-treated--

Claim 2, column 13, line 39, "heterpolyacid" should read --heteropolyacid--

Claim 3, column 14, line 26, "heterpolyacid" should read --heteropolyacid--

Claim 3, column 14, line 30, "of 1A" should read --of group 1A--

Claim 3, column 14, line 31, "the heat-treated periodic" should read --the periodic--

Claim 4, column 14, line 32, "heterpolyacid" should read --heteropolyacid--

Claim 5, column 14, line 38, "heterpolyacid" should read --heteropolyacid--

Signed and Sealed this

Twelfth Day of December, 2006

JON W. DUDAS
*Director of the United States Patent and Trademark Office*